United States Patent
Slattery et al.

(10) Patent No.: US 6,167,711 B1
(45) Date of Patent: Jan. 2, 2001

(54) SANITIZED ICE TRANSPORTATION SYSTEM AND METHOD

(75) Inventors: Larry Slattery; Jim L. Coffey, both of Oak Brook, IL (US)

(73) Assignee: Restaurant Technology, Inc., Oak Brook, IL (US)

(*) Notice: Under 35 U.S.C. 154(b), the term of this patent shall be extended for 0 days.

(21) Appl. No.: 09/293,185

(22) Filed: Apr. 16, 1999

(51) Int. Cl.[7] .................................................. F25C 5/18
(52) U.S. Cl. .................................................. 62/78; 62/344
(58) Field of Search ...................... 62/78, 344; 422/306; 406/46

(56) References Cited

U.S. PATENT DOCUMENTS

| | | | |
|---|---|---|---|
| 3,797,268 | 3/1974 | Garavelli | 62/258 |
| 3,877,241 | * 4/1975 | Wade | 62/344 |
| 4,104,889 | * 8/1978 | Hoenisch | 62/344 |
| 4,904,289 | * 2/1990 | Miyakami et al. | 62/78 |
| 5,329,950 | 7/1994 | Barinas | 134/95.3 |
| 5,354,152 | 10/1994 | Reinhardt et al. | 406/3 |
| 5,549,421 | 8/1996 | Reinhardt et al. | 406/3 |
| 5,586,439 | * 12/1996 | Schlosser et al. | 62/78 |
| 5,586,686 | 12/1996 | Bustos et al. | 221/211 |
| 5,587,087 | 12/1996 | Timmons | 210/724 |
| 5,636,710 | 6/1997 | Ables et al. | 186/41 |
| 5,761,908 | 6/1998 | Oas et al. | 62/3.2 |
| 5,783,537 | 7/1998 | Ahmed et al. | 510/193 |
| 5,803,377 | 9/1998 | Farrell | 241/36 |
| 5,816,443 | 10/1998 | Bustos | 221/211 |
| 5,845,504 | 12/1998 | LeBleu | 62/92 |
| 5,858,430 | 1/1999 | Endico | 426/241 |

* cited by examiner

Primary Examiner—William E. Tapolcai
(74) Attorney, Agent, or Firm—Ryndak & Lyerla

(57) ABSTRACT

A system and method is provided for making ice, transporting the ice to a remote location for subsequent use and for periodically sanitizing the transportation portion of the system without disabling or shutting down the system.

22 Claims, 4 Drawing Sheets

SANITIZED ICE TRANSPORTATION SYSTEM AND METHOD

FIELD OF THE INVENTION

The present invention relates to a system and method for making ice, transporting the ice to a remote location and sanitizing the ice transportation system. Specifically, the invention relates to introducing ozone gas into the ice transportation system and maintaining the ozone gas in the system for a sufficient time and at a sufficient concentration to sanitize the ice transportation system.

BACKGROUND OF THE INVENTION

Delivery systems for transporting ice from an ice source to a remote location are known. Typically, ice is made in the form of cubes by an ice maker. Then, the ice cubes are transported by the delivery system from the ice maker to a physically remote storage location. This storage location allows the ice to be used in conjunction with water, soft drink or other beverage dispensers.

In existing ice transportation or delivery systems, the delivery tube through which the ice is transported may become relatively moist or wet. This can be caused, in part, by some of the ice melting during conveyance or smaller chips of ice breaking off and then subsequently melting. A relatively wet, moist environment can be conducive to the growth of bacteria. The presence of bacteria in the delivery system is not desirable since it is possible that bacteria may come into contact with ice transported through the system. Consequently, a need exists for an effective method of sanitizing the distribution lines in an ice transportation system.

A practical and efficient ice delivery system that includes a sanitizing system that does not require the ice delivery system to be shut down and disassembled is needed, since completely shutting down the system is disruptive, inefficient and not otherwise desirable.

Disassembly and reassembly of the system is obviously inconvenient, time and labor intensive and results in substantial downtime. Moreover, even after completing the sanitation process and reassembling the equipment, the first batch of transported ice may have an unpleasant flavor or otherwise be wasted if residual amounts of the sanitizing agent are still in the lines. With ice, customers can often taste even a small amount of a foreign substance.

A need exists for a convenient and minimally labor intensive method for sanitizing an ice transportation system. A need also exists for a method and system for sanitizing all exposed surfaces in an ice transportation system.

For purposes of the present invention, the term "ice cube" includes all types, sizes and shapes of ice, including cubes, lumps and flakes. The term "ice cube" is also intended to include crushed ice.

For purposes of the present invention, the term "sanitizing" means the killing of bacteria, and as known to those skilled in the art, does not necessarily require the complete elimination of bacteria.

SUMMARY OF THE INVENTION

In one aspect of the present invention, there is provided a method and system for making and transporting ice to a remote location through a sanitized delivery system for storage or immediate use of the ice and sanitizing the ice delivery system in place. Typically, an ice storage container will be present at the remote location. The ice delivery system is sanitized by introducing ozone gas into the ice distribution system. The ozone gas is introduced in gaseous form into the atmosphere of the delivery system, which atmosphere typically will be ordinary air. By introducing the ozone in that manner, the ice delivery system can be readily sanitized in place without the necessity of disassembling or even shutting down the ice making and delivery system. Typically, the ice delivery system propels the ice by forced air or by mechanical conveyance structure.

The ozone gas may be introduced into the system by any suitable method, such as injection or introduction with an air blower or a venturi, for example. The ozone gas is then maintained in the ice distribution system for a sufficient time and at a sufficient concentration to sanitize the system. After sanitation, the ice distribution system will be substantially free of bacteria in the distribution system.

In accordance with another aspect of the invention, the interior exposed surfaces of the remote ice storage containers, which may be refrigerated, are also sanitized. After prolonged use, the remote ice storage containers also may become moist or wet during use, potentially could have bacteria present because, for example, the container interior is exposed to the outside atmosphere such as when ice is removed by a person. When the ozone gas is introduced into the system, it may be injected and maintained in the remote storage container to sanitize the interior exposed surfaces of the storage container.

In yet another aspect of the invention, the ice distribution system is sanitized regularly by periodic injection of ozone gas at predetermined time or ice delivery cycles. Thus, the sanitation process is periodically activated after a predetermined amount of time, such as about every 2–24 hours (for example, every 2, 4, 12 or 24 hours) or quantity of ice between cycles, such as after every 1 to 50 delivery cycles (for example, 1, 2, 5, 10 or 50 delivery cycles). In addition, an ozone concentration sensing device may be provided to monitor the concentration of ozone in the delivery system during the sanitizing cycle to ensure that a desired concentration of ozone for sanitizing is attained and for the desired time period.

In another aspect of the present invention, ozone gas is continuously injected into the ice distribution system, even when ice is being transported. This prevents bacteria from accumulating in the ice distribution system.

In yet another aspect of the present invention, the sanitation process is operated without any disassembly or shutting down of the ice distribution system. The ozone gas can be injected into the distribution lines at any time, such as between distribution cycles or even when the ice is being conveyed.

DETAILED DESCRIPTION OF THE INVENTION

Figure 1:
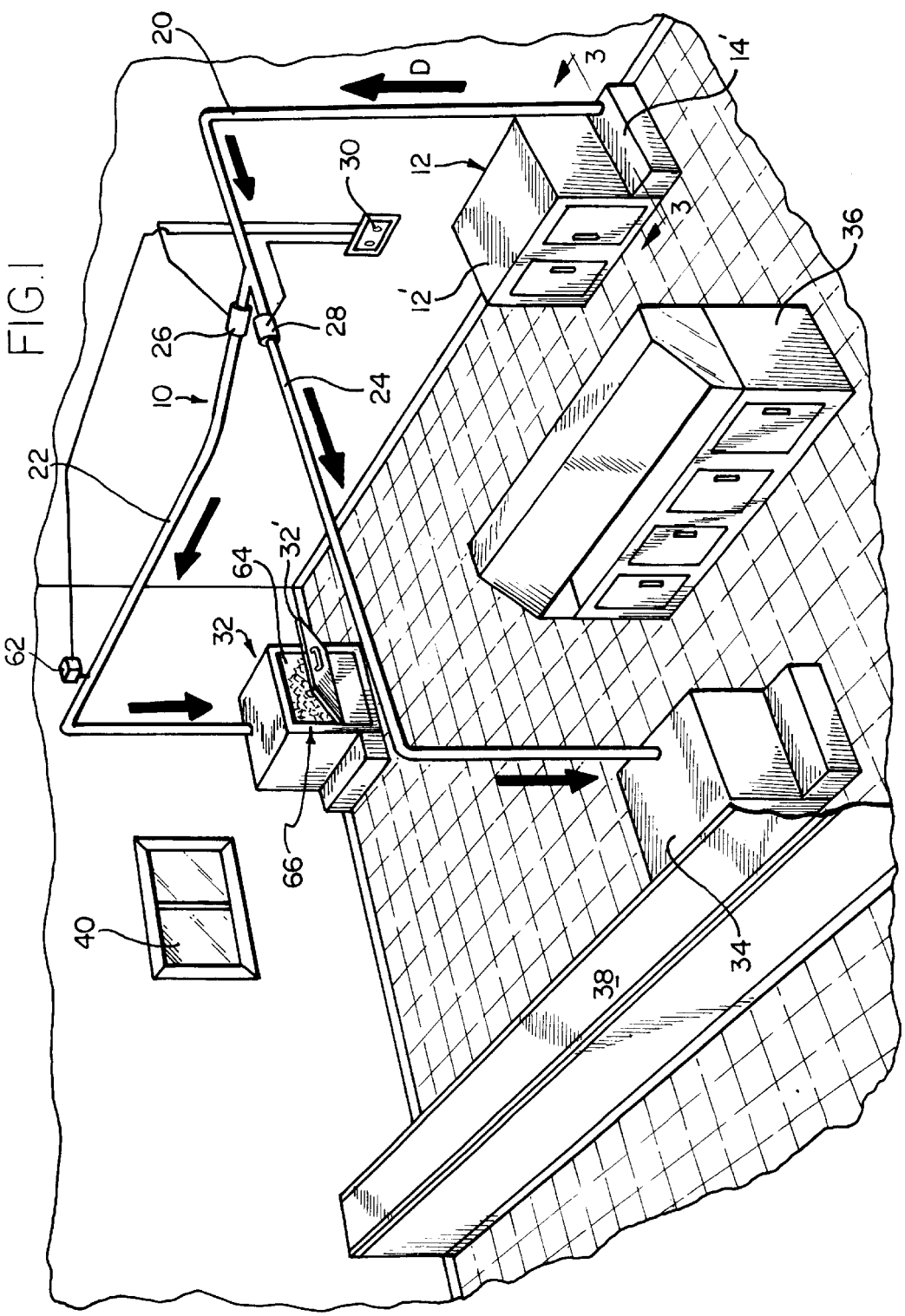
FIG. 1 is an elevation view of the ice making, distribution, storage, and sanitation equipment of the present invention.
Figure 3:
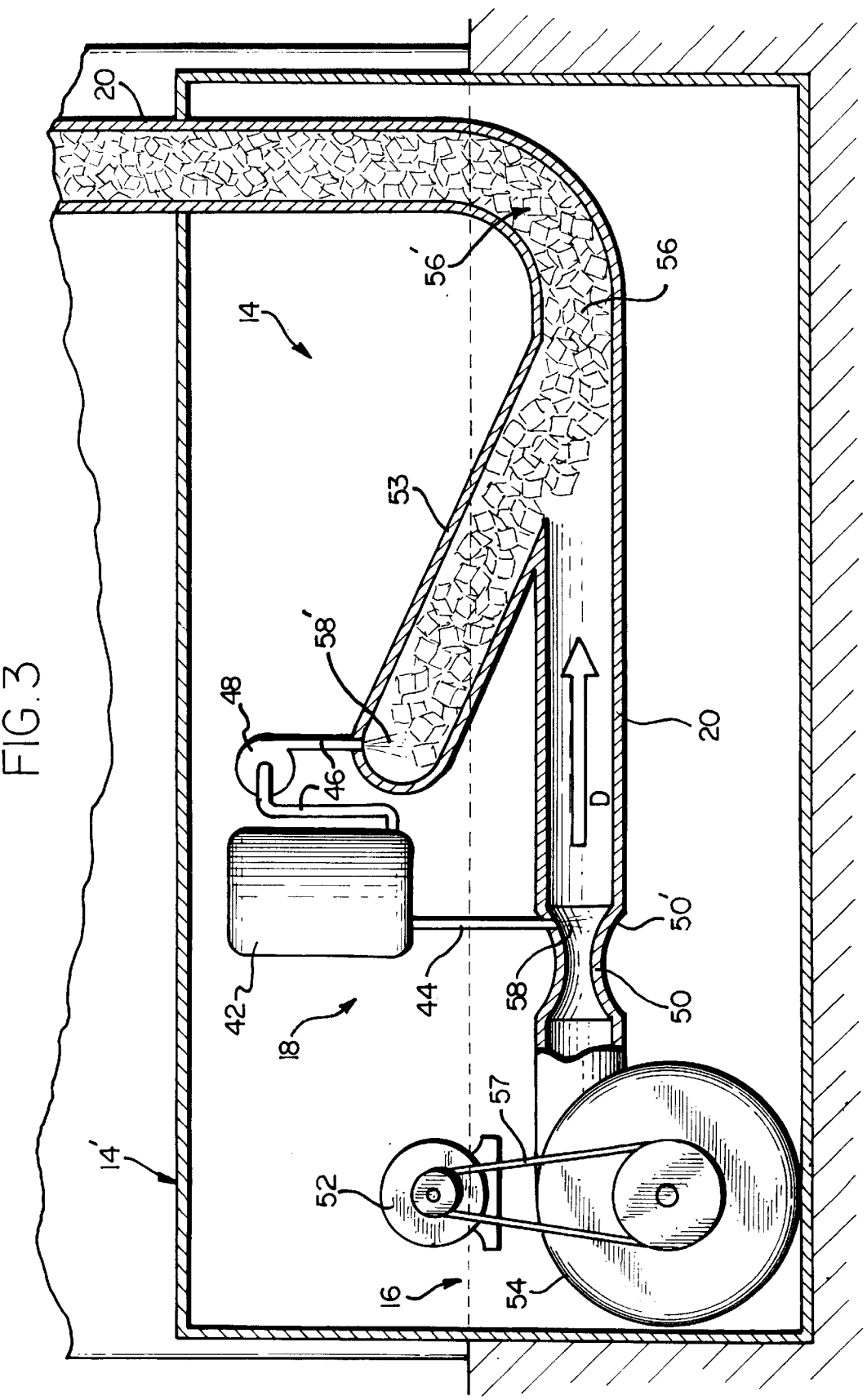
FIG. 3 is a sectional view of the sanitizing system of the present invention taken along line 3—3 of FIG. 1.

Referring to the drawings generally, and initially to FIGS. 1 and 3, there is illustrated an ice making, transporting, storing and sanitizing system 10 in accordance with the invention. System 10 is comprised of an ice maker 12 and an ice transport and sanitizing system 14, partially contained within enclosure 14' of FIG. 1, ozone generator and ozone injection system 18, distribution lines 20, 22 and 24, valves 26 and 28 and a control system 30. System 10 also includes ice storage containers 32 and 34.

System 10 is particularly suitable for a quick service restaurant where large quantities of ice are needed and where it is desired to convey ice from an ice maker (which can be in a remote store room, for example) located away from the main serving area to ice storage containers 32, 34 located near beverage dispensers 36 and service counter 38, for example. Alternatively, the ice may be conveyed to several different storage containers, such as near a drive-through window 40 which may also have a beverage dispenser located nearby (not shown) or in a location where customers may access the ice (not shown).

Although illustrated and described herein as transporting ice to two remote locations, ice may be distributed to only one or as many different locations as are desired. The present invention is suitable for sanitizing any such ice distribution system.

Ice maker 12 forms ice cubes and is schematically illustrated in FIG. 1 as being contained in a cabinet 12'. Any suitable ice making apparatus can be used in accordance with the invention. Ice maker 12 produces a plurality of pieces of ice 56 and may have the capacity to store a quantity of ice (not shown). Ice 56 is transported initially through distribution line 20 for subsequent distribution through lines 22 and/or 24. The ice may be transported in bulk such as in a slug 56' or piece by piece. Ice 56 is transported by means of compressed air provided by compressed air source 16 which can be any suitable source of compressed or forced air, such as a motor 52 that is connected to and drives a blower 54 through a belt 57. Alternatively, a direct drive (not shown) could be used in place of belt 57 to drive blower 54, for example. Any other suitable source of compressed or forced air could also be used.

Ozone injection system 18 includes an ozone generator 42, a main feed line 44, a secondary feed line 46, a secondary feed pump 48, and a venturi 50, all contained within enclosure 14'. Alternatively, ozone generator 42 may be located at a remote location. As a free-standing unit, it may be located in another area and merely transport the ozone into the ice transportation system. In any event, ozone generator 42 is coupled to distribution line 20 by main feed line 44. Ozone generator 42 forms gaseous ozone by any suitable method such as from oxygen and optionally can store quantities of ozone gas before or during a sanitation cycle. Ozone gas is believed to be an effective sanitizing agent because of its qualities as an oxidizer. Alternatively, the ozone gas formed by ozone generator 42 can be injected into distribution line 20 when desired by any suitable method.

Distribution lines 20, 22 and 24 connect ozone generator 42 and ice maker 12 to the remote storage containers. Although preferably there are two remote storage containers 32 and 34, there may be any desired number of remote storage containers at desired locations. If only one remote storage container is used, valves 26 and 28 are not necessary.

Distribution lines 20, 22 and 24 provide a path for ice to travel from ice maker 12 to the remote storage containers 32 and 34. Distribution lines 20, 22 and 24 are pipes of suitable internal diameter and preferably smooth internal surfaces to permit delivery of ice by compressed air. Any suitable type of pipe or other hollow conduit or passageway that allows the ice to be delivered by compressed air can be utilized. Distribution lines 22 and 24 may be made out of the same material as distribution line 20, and may be PVC pipe, for example. As shown in FIG. 3, ice 56 travels in direction D and typically will be conveyed by use of blown (compressed) air. Distribution line 20 branches into distribution lines 22 and 24 for delivery of ice to containers 32 and 34, respectively. Alternatively, a mechanical conveyor can be used to transport the ice through the distribution lines. In such embodiment, typically when the system is in the ice distribution or delivery mode, the mechanical conveyor will be on, and at other times, the conveyor will be off.

Valves 26 and 28 are used to regulate the flow of ice (and ozone gas, if present). Preferably, valves 26 and 28 are adjacent the point where distribution lines 22 and 24 diverge or branch from line 20 and lead to containers 32 and 34, respectively. Locating the valves adjacent with the branch in distribution lines prevents or minimizes ice from accumulating in a closed passageway and subsequently melting. When valves 26 and 28 are in the completely open position, ice will be conveyed to both remote storage containers 32 and 34. When valve 26 is closed, valve 26 prevents any ice in distribution line 20 from being conveyed to remove storage container 32 and ice is conveyed to container 34. When valve 26 is open and valve 28 is closed, ice is delivered only to container 32. Thus, if only one valve is open, then ice will only be conveyed to the remote storage container associated with that valve. This is useful if only one remote storage container needs ice or is in use. By regulating the amount each valve is open, one can regulate how much ice is delivered to each storage container. Typically, however, in the delivery mode, one valve will be open and one valve will be closed so that ice is delivered to only one storage container at a time.

Control system 30 is used to regulate valves 26 and 28 and to control the sanitizing cycle. Control mechanism 30 may be manually or automatically operated. Preferably, system 30 is configured so that when a demand for ice is made to deliver ice to container 32 or 34, the associated valve 26 or 28 is opened and the other valve is closed. A quantity of ice 56 is discharged from ice maker 12 and down delivery chute 53 which communicates with the end of line 20 adjacent compressed air source 16. The quantity of ice slug 56' may be a preselected amount and can be discharged by any suitable method, such as by gravity or a screw conveyor (not shown) from ice maker 12. The compressed air source is activated which transports ice slug 56' through lines 20 and either 22 or 24 to the selected storage container 32 or 34.

Control system 0 also controls and regulates the sanitizing cycle. Control system 30 includes a timer which periodically initiates the sanitizing cycle by activating ozone generator 42. Thereafter, compressed air source 16 is activated and ozone is introduced just downstream of compressed air source 16, into delivery chute 53 and through the distribution system, including lines 20, 22 and 24 and ice storage containers 32 and 34. Delivery of ozone into the distribution system can be through venturi 50 or by a pump 70, as hereinafter described. Compressed air source 16 may be operated at a lower output or flow rate when the sanitizing cycle is operating. The ozone delivery and flow of compressed air terminates when a sufficient amount of ozone is introduced or an ozone concentration is reached within lines 20, 22 and 24 of the distribution system which can be determined by ozone sensor 62 which communicates with control system 30. Alternatively, ozone can be continuously injected during the sanitizing cycle. After the ozone has remained in lines 20, 22 and 24 for a sufficient period of time for sanitizing, ozone injection is terminated and optionally compressed air source 16 is operated to purge lines 20, 22 and 24 and containers 32 and 34 of ozone.

Remote storage containers 32 and 34 store the ice before it is used, for example, as beverage ice or for some other purpose as desired. Containers 32 and 34 are physically removed from ice maker 12. Typically, containers 32 and 34 are insulated and may also be refrigerated. Access to containers 32 and 34 is provided by a suitable door, for example, such as door 32' of container 32. The storage containers may be close to beverage dispensers or in locations where a customer may have access to them. Containers 32 and 34 have interior surfaces 64 (shown only with respect to container 32) that define the ice storage bin portion 66 of container 32. Exposed interior surfaces 64 may be contacted by ozone gas during the sanitizing cycle. Preferably, containers 32 and 34 have little or no ice therein during sanitation for maximum contact of surfaces 64 with ozone.

A compressor, blower, pump, venturi or other device can be used to inject the ozone gas into the distribution lines when desired. The compressor or other device may be present adjacent to the ice maker or as a remote source. The blower moves the ozone gas into the distribution lines. As the ozone gas is introduced in the distribution line, it sanitizes all or substantially all of the exposed area it contacts. By closing valve 26, valve 28 or both, selective areas of the equipment can be sanitized. The ozone gas also sanitizes the interior surfaces of remote storage containers 32 and 34 that define the ice storage bin portion thereof if the associated valve 26 or 28 is not closed, such as surfaces 64 that define bin portion 66 of container 32.

The embodiments disclosed in FIGS. 3 and 4 will now be described in more detail. Specifically referring to FIG. 3, there is illustrated a sectional view along lines 3—3 of FIG. 1 of ice maker 12 and the portion of ice transport and sanitizing system 14 contained in housing 14'. In the embodiment illustrated in FIG. 3, venturi 50 is utilized to introduce ozone gas 58 into line 20. Main ozone feed line 44 communicates with the low pressure downstream side 50' of venturi 50 which draws ozone gas 58 therein when blower 54 and ozone generator 42 is operated. Optionally, ozone generator 42 also supplies ozone gas 58' to ice delivery chute 53 through secondary ozone feed line 46 and pump 48.

Figure 4:
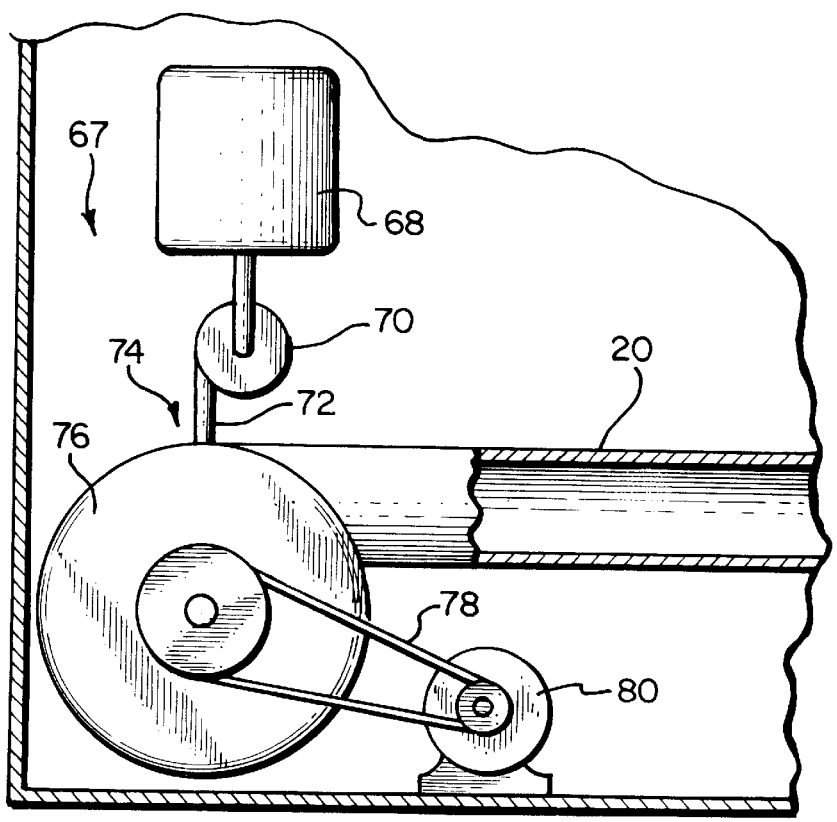
FIG. 4 is a sectional view of an alternative embodiment of the sanitizing system of the present invention.

Referring to FIG. 4, there is illustrated an alternate ozone injection apparatus 67 composed of ozone generator 68, an ozone injection pump 70 which injects ozone gas through line 72 into the intake 74 of blower 76, which is driven through a belt 78 by motor 80. Alternatively, pump 70 and line 72 could be connected directly to line 20 downstream of blower 76 for injection of ozone gas at that location, if desired. Ice cubes 56 are introduced from ice maker 12 to line 20 via delivery chute 53. The ozone gas 58 (and ice cubes 56 if present) travel downstream along direction D from lines 20 and 53 into and through distribution lines 20, 22 and 24. Although the system is illustrated with ice being present at the same time that ozone gas is being injected, this is typically not the case.

The ozone gas is maintained in the distribution lines at a sufficient concentration until the lines are appropriately sanitized. Because the ozone is in its gas phase, it is able to expand easily and contact all exposed surfaces of the lines. Typically, the sanitizing process is operated when there is no ice present in the distribution lines, although it may be operated during the ice distribution process. When the ozone gas is being maintained in the distribution lines, the gas contacts all internal portions of the ice delivery system. Ozone's strong oxidizing activity sanitizes the system. Optionally, after the sanitation process is complete, the ozone gas is removed from the system. This can be accomplished by, for example, activating blower 54 or by providing a vacuum in containers 32 and 34 or at the terminal (container) end of lines 22 and 24, such as by vacuum sources 82 and 84 shown in FIG. 2.

Depending upon, among other things, the temperature of the distribution lines and the acceptable post-sanitation level of bacteria, the residence time and concentration of the ozone gas vary. The ozone gas should be maintained in the system for a sufficient time and at a sufficient concentration to effect a desired level of sanitation. The ice maker 12 or remote storage containers 32 and 34 do not need to be disconnected prior to sanitation. In fact, none of the pieces of equipment needs to be disconnected prior to sanitation, nor must ice maker 12 or ice transport system 14 be shut down, which is a significant advantage of the present invention.

As previously described, ozone gas may be injected into one or more of the remote storage containers 32 and 34. By maintaining the ozone gas in the remote storage container for a sufficient time and at a sufficient concentration, all exposed surfaces of the container, such as surfaces 64 of container 32 can be sanitized.

The ice distribution system may be sanitized as often as necessary or desired. Depending upon the use of the system and other conditions, the sanitation cycle may be set to automatically run every 2, 4, 8, 12 or 24 hours or otherwise as desired, for example. The sanitation process may also be used whenever it is desired to sanitize the distribution line.

It is also understood that ozone may be continuously injected into the system or periodically injected semi-continuously between relatively short time intervals, if desired. Ozone injection could occur even when ice is present in the distribution lines. In a continuous or semi-continuous injection mode, generally a lower concentration of ozone gas will be needed for sanitation than for less frequent ozone injection.

Figure 2:
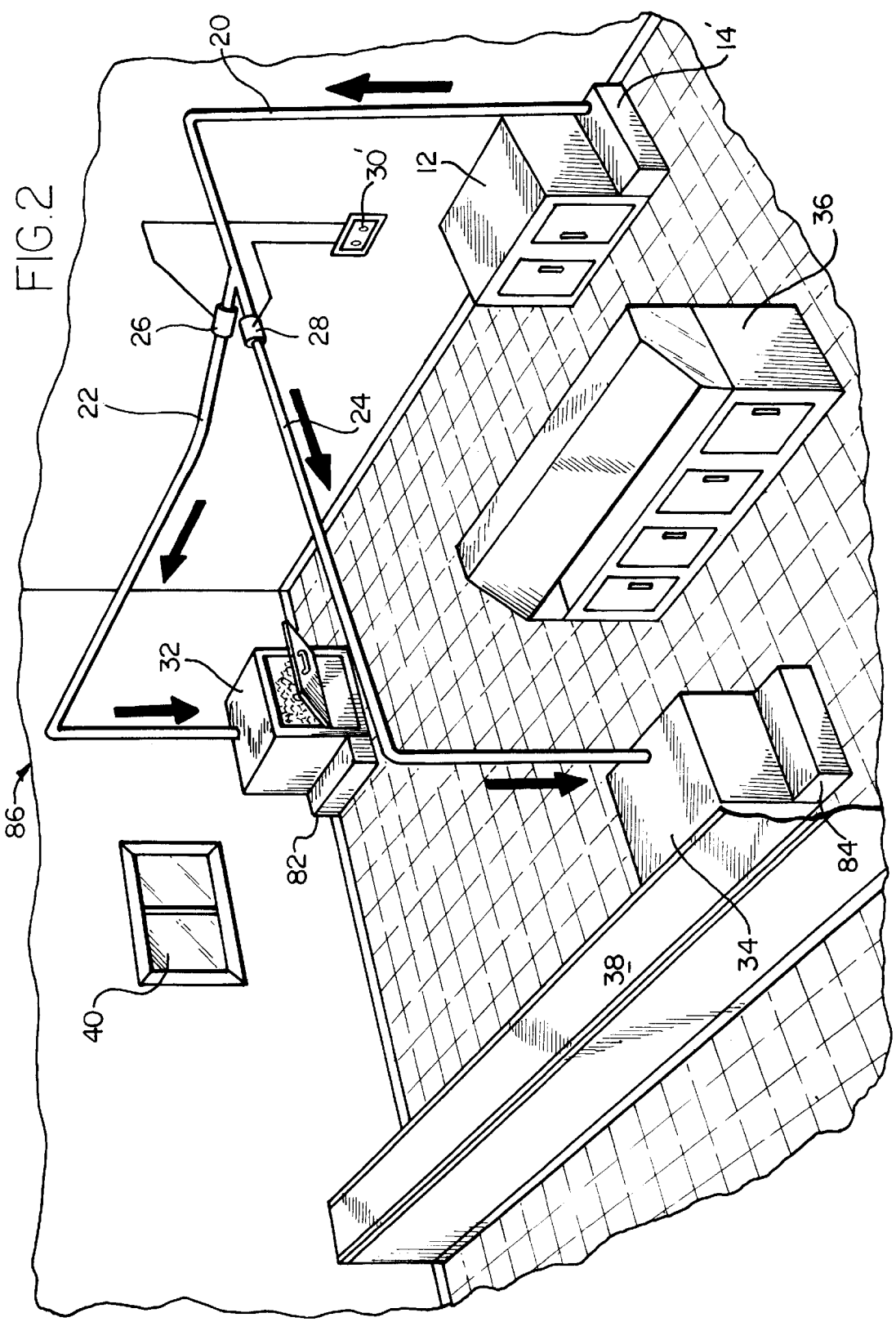
FIG. 2 is an elevation view of an alternative embodiment of the sanitizing system of the present invention.

Referring to FIG. 2, there is illustrated an alternative embodiment of the present invention. System 86 is comprised of ice maker 12, an ozone generator located in housing 14' that communicates with line 20 in housing 14', distribution lines 20, 22 and 24, valves 26 and 28, control system 30' (similar to control system 30), storage containers 32 and 34 and vacuum sources 82 and 84. Similar to system 10, system 86 functions to distribute ice from ice maker 12 to storage containers 32 and 34. Vacuum sources 82 and 84 are used to draw ozone gas through the distribution lines 20, 22 and 24. Vacuum sources 82 and 84 may be any device that can provide suction into the distribution lines sufficient to draw ozone gas through lines 20, 22 and 24. Additionally, vacuum sources 82 and 84 can be used to remove the ozone gas from system 86 after completion of the sanitation process. After evacuation, none or substantially none of the ozone gas is present in the distribution lines 20, 22 and 24.

Figure 5:
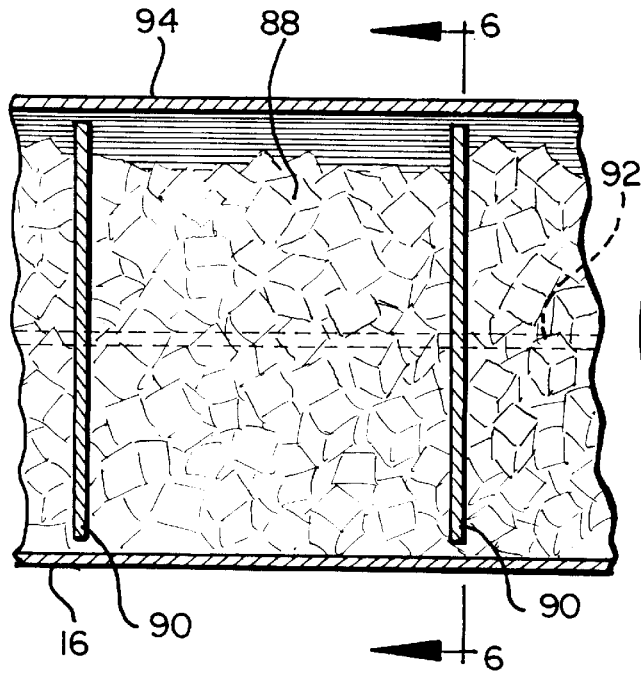
FIG. 5 is a sectional view of an embodiment of the distribution line of transporting ice of the present invention.
Figure 6:
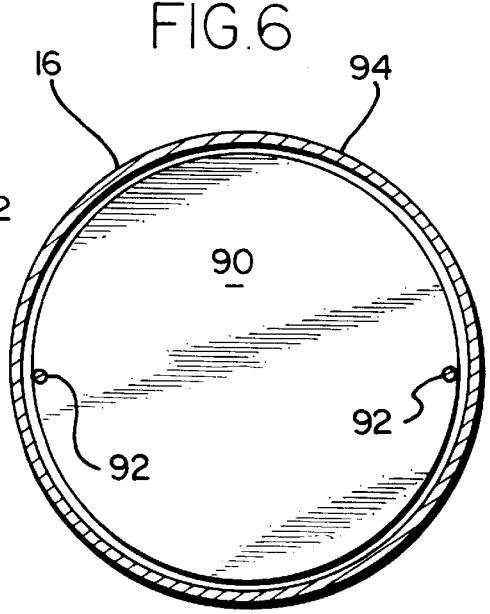
FIG. 6 is a perspective view of the ice distribution line taken along line 6—6 of FIG. 5.

Finally, referring to FIGS. 5 and 6, there is illustrated a portion of an endless loop mechanical conveyor system of conveying ice through a distribution line 94. A conveyor is provided consisting of a plurality of spaced apart circular conveyor divider members 90 attached to cables 92, which are connected to a drive mechanism (not shown). When cables 92 are pulled through distribution line 94, divider members 90 follow, thereby providing a conveyor. Quantities of ice cubes 88 are separated by circular divider members 90. Circular divider conveyor members 90 have a diameter that is slightly smaller than the internal diameter of line 94. Quantities of ice cubes 88 typically are located between dividers 90. As divider members 90 move, they transport ice cubes 88 through the distribution line.

While the invention has been described with respect to certain preferred embodiments and, as will be appreciated by those skilled in the art, it is to be understood that the invention is capable of numerous changes, modifications and rearrangements and such changes, modifications and rearrangements are intended to be covered by the following claims.

We claim:

1. A system for making ice, distributing the ice to a remote location and sanitizing the ice distribution system comprising:
    a) an ice maker capable of forming a plurality of pieces of ice;
    b) a remote storage container that is physically removed from the ice maker for storing pieces of ice from said ice maker;
    c) a distribution line communicating with the ice maker and the remote storage containers for distributing the pieces of ice from the ice cube maker to the remote storage location;
    d) an ozone generator for generating gaseous ozone coupled to the distribution line;
    e) means for injecting the gaseous ozone generated by the ozone generator into the distribution line in a sufficient quantity to sanitize the distribution line; and
    f) means for distributing the gaseous ozone through the distribution line and maintaining the ozone in the distribution line for a time and concentration sufficient to sanitize the distribution line.

2. The system of claim 1 wherein the means for injecting the gaseous ozone includes means for periodic ozone injection at predetermined time intervals.

3. The system of claim 1 wherein the means for injecting the gaseous ozone includes means for continuous injection of ozone.

4. The system of claim 1 wherein the means for injecting the gaseous ozone comprises a pump.

5. The system of claim 1 wherein the means for injecting the gaseous ozone comprises a venturi.

6. The system of claim 1 wherein the means for distributing the gaseous ozone is a vacuum source.

7. The system of claim 1 wherein the distribution line comprises a pipe.

8. The system of claim 1 further comprising means to sense the ozone concentration.

9. The system of claim 1 wherein the distribution line comprises a conveying apparatus.

10. The system of claim 1 wherein the remote storage container is sanitized by the ozone gas.

11. A system for making ice, distributing the ice to a remote location and sanitizing the ice distribution system comprising:
    a) an ice maker capable of forming a plurality of pieces of ice;
    b) a transportation system for transporting the plurality of pieces of ice from the ice cube maker to a remote location;
    c) an ozone source providing gaseous ozone; and
    d) means for injecting and distributing the gaseous ozone in the transportation system for a sufficient time and at a sufficient concentration to sanitize the transportation system.

12. The system of claim 11 wherein the gaseous ozone is injected and distributed by an air blower.

13. A sanitation system for sanitizing an ice transportation system comprising:
    a) an ozone source for providing gaseous ozone into a distribution line between an ice maker and a remote location;
    b) injection means for providing the gaseous ozone from the ozone source into the distribution line for a sufficient time and at a sufficient concentration to sanitize the distribution line; and
    c) removal means to substantially evacuate the gaseous ozone from the distribution line after the distribution line has been sanitized.

14. A method of sanitizing an ice delivery system composed of an ice delivery tube extending from an ice maker to a remote location comprising:
    a) periodically injecting ozone gas into the ice delivery tube;
    b) transporting the ozone gas through the delivery tube; and
    c) maintaining the ozone gas in the tube at a concentration and for a time sufficient for sanitizing the tube.

15. The method of claim 14 wherein the ozone gas is injected into the delivery tube at predetermined time intervals.

16. The method of claim 14 wherein the ozone gas is injected into the delivery tube at least every 24 hours.

17. The method of claim 14 wherein the ozone gas is injected into the delivery tube at least every 12 hours.

18. The method of claim 14 wherein the ozone gas is injected into the delivery tube at least every 4 hours.

19. The method of claim 14 comprising the additional step of thereafter removing the ozone gas from the delivery tube.

20. The method of claim 14 further comprising sensing the concentration of ozone in the delivery tube; and continuing the injection of ozone until a minimum desired ozone concentration is achieved.

21. A method of sanitizing an ice transportation system composed of an ice delivery tube extending from an ice maker to a remote location comprising:
    a) periodically injecting ozone gas into the ice delivery tube; and
    b) maintaining the ozone gas in the delivery tube at a concentration and for a time sufficient for sanitizing the tube.

22. The method of claim 21 wherein the ozone gas is injected into the ice delivery tube without the tube being disconnected from the system.

* * * * *

UNITED STATES PATENT AND TRADEMARK OFFICE
CERTIFICATE OF CORRECTION

PATENT NO. : 6,167,711 B1
DATED : January 2, 2001
INVENTOR(S) : Larry Slattery, Jim L. Coffey It is certified that error appears in the above-identified patent and that said Letters Patent is hereby corrected as shown below:

<u>Column 4,</u>
Line 53, delete "0" and insert therefor -- 30 --.

Signed and Sealed this

Second Day of October, 2001

Attest:

*Nicholas P. Godici*

NICHOLAS P. GODICI
*Attesting Officer           Acting Director of the United States Patent and Trademark Office*